US008892365B2

(12) United States Patent  
Richmond et al.

(10) Patent No.: US 8,892,365 B2  
(45) Date of Patent: *Nov. 18, 2014

(54) OPTIMIZED PROBE SELECTION METHOD

(71) Applicant: Ventana Medical Systems, Inc., Tucson, AZ (US)

(72) Inventors: Todd Richmond, Madison, WI (US); Jason Norton, Madison, WI (US); Emile F. Nuwaysir, Madison, WI (US); Roland Green, Madison, WI (US); Kate Nuwaysir, Madison, WI (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/767,207

(22) Filed: Feb. 14, 2013

(65) Prior Publication Data

US 2014/0031244 A1 Jan. 30, 2014

Related U.S. Application Data

(63) Continuation of application No. 12/963,076, filed on Dec. 8, 2010, now abandoned, which is a continuation of application No. 11/346,927, filed on Feb. 3, 2006, now Pat. No. 7,869,959.

(60) Provisional application No. 60/650,265, filed on Feb. 4, 2005.

(51) Int. Cl.  
*G06F 19/20* (2011.01)  
*C12Q 1/68* (2006.01)

(52) U.S. Cl.  
CPC ............ *C12Q 1/6837* (2013.01); *C12Q 1/6811* (2013.01); *G06F 19/20* (2013.01)  
USPC .............................................. 702/20; 435/6.1

(58) Field of Classification Search  
CPC ..... G06F 19/20; C12Q 1/6811; C12Q 1/6813  
See application file for complete search history.

(56) References Cited

U.S. PATENT DOCUMENTS

| 5,143,854 | A | 9/1992 | Pirrung et al. |
| 6,375,903 | B1 | 4/2002 | Cerrina et al. |
| 7,869,959 | B2 * | 1/2011 | Richmond et al. .............. 702/19 |
| 2002/0048763 | A1 * | 4/2002 | Penn et al. ........................ 435/6 |
| 2002/0133301 | A1 | 9/2002 | Hubbell |
| 2004/0009484 | A1 | 1/2004 | Wolber et al. |
| 2004/0101846 | A1 | 5/2004 | Collins et al. |

FOREIGN PATENT DOCUMENTS

| WO | 0105935 A2 | 1/2001 |
| WO | 0242485 A2 | 5/2002 |
| WO | 03087993 A2 | 10/2003 |

OTHER PUBLICATIONS

Draghici et al. Reliability adn reproducibility issues in DNA microarray measurements Trends in Genetics vol. 22, pp. 101-109 (2006).*  
Mei et al. Probe selection for high-density oligonucleotide arrays Proceedings of the National Academy of Sciences USA vol. 100, pp. 11237-11242 (2003).*  
Chou, et al., "Optimization of probe length and the number of probes per gene for optimal microarray analysis of gene expression," Nucleic Acids Research, 2004, vol. 32, No. 12, e99, 8 pages.  
Hubbell, et al., "Robust estimators for expression analysis," Bioinformatics, vol. 18, No. 12, 2002, pp. 1585-1592.  
Ramdas, et al., "Sources of nonlinearity in cDNA microarray expression measurements," Genome Biology 2001, 2 (11): research0047.1-0047.7.  
Singh-Gasson, et al., "Maskless fabrication of light-directed oligonucleotide microarrays using a digital micromirror array," Nature Biotechnology, vol. 17, Oct. 1999, pp. 974-978.

* cited by examiner

*Primary Examiner* — John S Brusca  
(74) *Attorney, Agent, or Firm* — Ventana Medical Systems, Inc.

(57) ABSTRACT

The present invention provides methods for optimizing oligonucleotide hybridization probes for use in basic and clinical research. Specifically, the invention involves hybridizing serially diluted genomic sample to the oligonucleotide probes on the array, such that a signal intensity is produced for each of the probes; computationally identifying optimized probes which exhibit signal intensities that correspond to the serial dilutions of genomic sample and are reproducibly strong relative to non-optimized probes.

5 Claims, 4 Drawing Sheets

OPTIMIZED PROBE SELECTION METHOD

CROSS-REFERENCE TO RELATED APPLICATIONS

This application is a continuation application of U.S. application Ser. No. 12/963,076, filed Dec. 8, 2010, which is a continuation application of U.S. application Ser. No. 11/346,927, filed Feb. 3, 2006, now issued as U.S. Pat. No. 7,869,959, which claimed the benefit of U.S. Provisional Application No. 60/650,265, filed Feb. 4, 2005. Each document is incorporated herein by reference as if set forth in its entirety.

STATEMENT REGARDING FEDERALLY SPONSORED RESEARCH OR DEVELOPMENT

Not Applicable

BACKGROUND OF THE INVENTION

The advent of DNA microarray technology makes it possible to build an array of hundreds of thousands of DNA sequences in a very small area, such as the size of a microscopic slide. See, e.g., U.S. Pat. Nos. 6 375,903 and 5,143,854, each of which is hereby incorporated by reference in its entirety. The disclosure of U.S. Pat. No. 6,375,903, also incorporated by reference in its entirety, enables the construction of so-called maskless array synthesizer (MAS) instruments in which light is used to direct synthesis of the DNA sequences, the light direction being performed using a digital micromirror device (DMD). Using an MAS instrument, the selection of DNA sequences to be constructed in the microarray is under software control so that individually customized arrays can be built to order. In general, MAS based DNA microarray synthesis technology allows for the parallel synthesis of over 786,000 unique oligonucleotides in a very small area of a standard microscope slide. The microarrays are generally synthesized by using light to direct which oligonucleotides are synthesized at specific locations on an array, these locations being called features. Typically, one nucleotide sequence is synthesized at each feature of the array, i.e., there are multiple probes in each feature, but all those probes have the same nucleotide sequence. For certain applications, oligonucleotides of different sequences can be present within one feature of the array, and the ratio and direction (5'-3', or 3'-5') of these oligonucleotides can be controlled.

With the availability of the entire genome of hundreds of organisms, for which a reference sequence has generally been deposited into a public database, microarrays have been used to perform sequence analysis on DNA isolated from such organisms. Microarray methods that for example, allow the measurement of changes in DNA copy number are useful for the determination of chromosomal aberrations in higher eukaryotes that are often linked to disease states. Changes in copy number are typically the result of amplification or deletions of stretches of chromosomes. While large amplification and deletion or translocations can be readily detected by traditional karyotyping methods, the amplification or deletion of smaller DNA fragments within a chromosome can be difficult or impossible to detect by these methods. Accordingly, it has become increasingly important for genetic analysis to utilize the most accurate oligonucleotide probes.

Recently, several research groups have developed methods to optimize probes. For example, to avoid cross-hybridization of highly similar sequences on a microarray, researchers have developed an approach to determine the optimal number and length of gene-specific probes for accurate transcriptional profiling studies. The study surveyed probe lengths from 25 to 1000 nt. It was found that long probes yielded a better signal intensity than short probes. However, the signal intensity of short probes could be improved by addition of spacers or using higher probe concentration for spotting. (see Chou et al., Optimization of probe length and the number of probes per gene for optimal microarray analysis of gene expression. *Nucleic Acids Res.* 2004 Jul. 8; 32 (12):e99.) It is believed that alternative methods for optimizing probes for use in identifying genetic modifications would be a desirable contribution to the art.

BRIEF SUMMARY OF THE INVENTION

The present invention is summarized as a method for optimizing oligonucleotide hybridization probes for use in basic and clinical research. The premise behind this optimization strategy is that probes which exhibit signal intensities corresponding to serial dilutions of a genomic sample, and which exhibit strong and consistent signal intensity are well suited for use as optimized probes for a variety of hybridization techniques. In particular the invention provides a method for optimizing oligonucleotide probes for use in microarray hybridization techniques. The method includes providing a plurality of oligonucleotide probes on a hybridization array; providing serial dilutions of a genomic sample, wherein the genomic sample is labeled; hybridizing the labeled and serially diluted genomic sample to the probes on the array, such that a signal intensity is produced for each of the probes, wherein the hybridization step is performed at least one time; computationally generating weighted regression data from the signal intensity produced for each of the probes, identifying optimized probes using a probe selection algorithm; wherein the probes exhibit signal intensities that correspond to the serial dilutions of genomic sample, are reproducible and strong relative to non-optimized probes.

One aspect of the invention provides that the oligonucleotide probes are either DNA or RNA.

In another aspect, the invention provides a method for the optimization of probes for any hybridization based assay including microarrays, bead-based assays, genotyping assays and RNAi assays.

A further aspect of the invention is to use the method of the invention in optimizing probes used in the fields of genomics, pharmacogenomics, drug discovery, food characterization, genotyping, diagnostics, gene expression monitoring, genetic diversity profiling, RNAi, whole genome sequencing and polymorphism discovery, or any other applications involving the detection of genetic alteration involving an amplification or deletion in a chromosome.

Other objects advantages and features of the present invention will become apparent from the following specification.

DETAILED DESCRIPTION OF THE INVENTION

Figure 1:
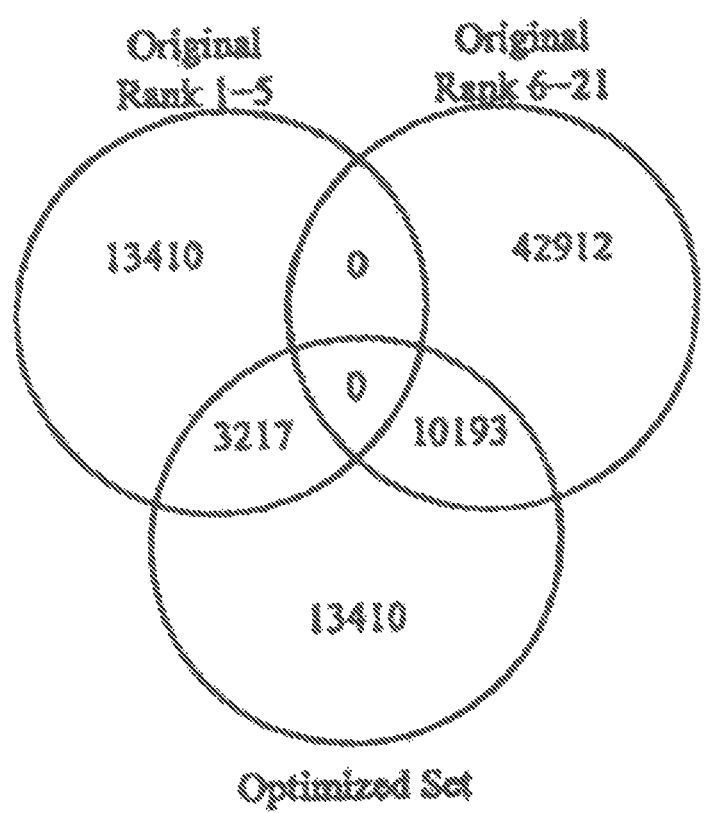
FIG. 1 is a Venn diagram showing a comparison of original and optimal probe sets indicating that the initial in silico rank selection may be improved by the empirical hybridization data.

The present invention relates to a method for optimizing oligonucleotide probes for a variety of basic research and medical applications. The premise behind this optimization strategy is that probes which exhibit signal intensities corresponding to serial dilutions of a genomic sample, and which exhibit strong and reproducible signal intensity are best suited for use as optimized probes for a variety of hybridization techniques. In particular the invention provides a method for optimizing oligonucleotide probes for use in microarray hybridization techniques. The method includes providing a plurality of oligonucleotide probes on a hybridization array; providing serial dilutions of a genomic sample, wherein the genomic sample is labeled; hybridizing the labeled and serially diluted genomic sample to the probes on the array, such that a signal intensity is produced for each of the probes, wherein the hybridization step is performed at least one time; computationally generating weighted regression data from the signal intensity produced for each of the probes, identifying optimized probes using a probe selection algorithm; wherein the probes exhibit signal intensities that correspond to the serial dilutions of genomic sample, are reproducible, and strong relative to non-optimized probes.

In one embodiment, the present invention provides a method for identifying and selecting optimized probes for use in hybridization experiments. In practicing the invention, the genomic sample (labeled and serially diluted) is hybridized to oligonucleotide probes on a microarray such that a signal intensity is generated. By "genomic sample," it is meant any source, including plants, animals, such as mammals, embryonic, new-born, adult humans, recombinant genomes, stem cells, human solid tumor cell lines and tissue samples.

By labeling the genomic sample, it is meant end-labeling with biotin. Alternatively, those skilled in the art would appreciate that other labeling methods could be equally suitable in practicing the invention. Also, while the present invention is not limited to a particular set of hybridization conditions, in a preferred embodiment of the invention, the hybridizations are performed in a MES based buffer (pH 6.6), under stringent conditions at 45° C. for 16-18 hrs.

A weighted linear regression was then fitted to the dilution series for each oligonucleotide probe and the slope and correlation coefficients are calculated. A log2 transformation of the signal intensity and a weighted linear regression are used to minimize the effect of outliers on the data. The weights for the linear regression are calculated by fitting the line, calculating the residuals, and then using the weights from a tukey biweight mean calculation (see Hubbel, et al., Robust estimators or expression analysis, *Bioinformatics* 2002 December; 18(12):1585-92) on the residuals to fit a weighted regression. At the same time, the tukey biweight mean of the signal intensities of the probe at the 4× dilution was calculated to represent the overall signal intensity of the probe. Table 1, shown below provides a description of the information required for identifying optimized probes.

TABLE 1

| COLUMN_NAME | DESCRIPTION |
| --- | --- |
| SEQ_ID | Unique identifier for sequence ID |
| PROBE_ID | Unique identified for probe ID |

TABLE 1-continued

| COLUMN_NAME | DESCRIPTION |
| --- | --- |
| POSITION | Position of probe in parent sequence |
| WEIGHTED_SLOPE | Weighted slope of dilution series |
| WEIGHTED_R_SQUARED | Weighted correlation coefficient |
| INTENSITY | Tukey biweight mean of signal intensity from 4X dilution. |

The weighted regression data is loaded into a MySQL relational database (available through MySQL AB) and probes are selected using a modification of the rank selection algorithm available through NimbleGen Systems, Inc., Madison, Wis. The rank selection algorithm is described in the experimental design exemplified herein below. The modification is the change in scores. For example, instead of uniqueness criteria, the data used is obtained from the hybridization. The weights for the various pieces of data are described herein below. In a typical embodiment, the method is performed by submitting a query to the database and gathering all of the information for the probes for a given SEQ ID. Next, a first pass is made through the probes to calculate an initial score. The first pass is the calculation of the initial score for each probe and the actual selection of the first probe. This initial score is calculated using the following weights:

Weighted slope*100
Weighted correlation coefficient*100
Intensity*6
−3*Log2(Distance form 3' end)=positional weight The goal is to have each of the major components contribute approximately ⅓ of the final score, and have the positional weight play a more minor role since the initial probe selection process should have adequately spaced the probes. A probe perfectly matching the dilution series of the genomic sample will have a slope of 2 (4-fold dilution in log2 space). Therefore, the maximum contribution from slope is 200. However, very few of the probes exceed a value of 1. This is not uncommon—signal intensity does not track perfectly with DNA concentration. An unresponsive probe will have a slope of 0. Probes can have negative slopes—these will add a negative value to the score, thus selecting against these probes. Thus the minimum contribution from slope is −200. However, an effective range based on experimentation is −100 to about 100.

Similarly, the correlation coefficient ($r^2$) can range from 0 (no correlation) to 1 (perfect correlation). Thus, the range of contributions from the correlation coefficient is about 0 to 100. For signal intensity, the data from a 16-bit TIFF image can range from 1 to 65536. In log2, the range is from 0 to 16, so multiplying by 6 gives a range of 0 to 96.

For the positional weight, the maximum sequence length for a transcript in, for example, a bacterial genome is unlikely to be much longer than 8196 by ($2^{19}$), so the maximum penalty for distance from the 3' end is −3*log2 (8196 bp)=−39. A probe at the 3' end would have no penalty so the range of contributions from position will be between 0 and −39. Most bacterial transcripts are, on average, going to be less than a thousand base pairs, so the range is more realistically between about 0 and −30.

After the initial score calculation, the probe with the highest score is selected as the $1^{st}$ ranked probe. Subsequent passes can be performed, recalculating the score by adding a bonus for probes that are farthest from previously selected probes, instead of penalty for distance from the 3' end. If the location of the first probe selected is at the 3' end in the longest transcript, then the maximal bonus would be the same as the initial penalty, so the position bonus will again range from 0 to approximately 30. As more probes are selected, however, the maximum bonus must necessarily decrease as the intervals between selected probes decreases. Therefore, all other data values being equal, scores will decrease with each successive probe selection.

The following examples are provided as further non-limiting illustrations of particular embodiments of the invention.

EXAMPLE

In a preferred embodiment of the invention, the goal was to start with an initial set of twenty-one 24-mer probes for each of the 2682 genes in Lactococcus lactis subsp. cremoris SK11, and after performing the novel probe optimization method described herein to select the top 5 probes for each gene placed in a single 13000 feature well of NimbleScreen 12plex format (available through NimbleGen Systems, Inc.).

Experimental Design

Lactococcus lactis subsp. cremoris SK11 Probes

In designing the experiment, standard NimbleGen rank selection was used to select twenty-one 24-mer probes from each of 2682 sequences in Lactococcus lactis subsp. cremoris SK11 probes for use as the initial probe set. The standard rank selection is an interactive, score based process that is used to select hybridization probes based on 4 parameters. The initial score is calculated using the following four parameters.

Weighted uniqueness*100. By the term "weighted uniqueness" it is meant a Boolean (0 or 1) measure of whether the 24-mer oligonucleotide is 3 weighted mismatches away from every other 24-mer oligonucleotide in the target genome. This measure is separate from an exact 24-mer match to another oligonucleotide.

(24-mer frequency−1)*−10. 24-mer oligonucleotides that have more than 1 exact match in the target genome are penalized.

Base pair composition score*50. The base pair composition score is a Boolean measure of whether the 24-mer oligonucleotide passes a number of rules based on the base pair composition of the oligonucleotide, runs of homopolymer bases, and a self-complementary score.

Positional weight equal to −10*Log2 distance of the probe from the 3' end of the sequence or transcript. After the first probe for each sequence is selected, the positional weight is altered to a bonus dependent on the distance to the nearest selected probe, which as a result forces even spacing across the target sequence.

E. coli Probes

E. coli K12 probes were selected as intensity normalization controls. A total of 6044 E. coli probes were selected as follows: Probes were tiled at a 10 base pair interval throughout the entire E. coli K12 genome. This probe set was run through NimbleGen System, Inc.'s standard probe selection pipeline (as described above) to collect probe information, using both the forward and reverse strands of the L. cremoris genome as the uniqueness target. Instead of the normal rank selection process, however, a simple filter was applied to include only probes that could be synthesized in 72 cycles or less; did not appear as an exact match in the L. cremoris genome; and were 3 weighted mismatches away from any L. cremoris 24-mer.

Random GC probes

Random probes (1900) of defined GC contents (6-14%) were placed on the array as low-end intensity normalization controls. The GC percentage was calculated based on the mean GC content (+/−2 standard deviations) of the L. cremoris probes on the array.

Layout

The optimization design was performed on the standard NimbleGen expression platform, 385,000 features with 1:2 feature format density, with no mismatches. To compensate for possible uniformity issues on the array, the probes were arranged in vertical stripes on the array, for a total of 6 replicate sets. Each set of probes/controls was placed randomly in overlapping named containers (ECOLI_BLOCK1, LCRE_BLOCK1, RANDOM_BLOCK1, etc.).

Labeling

Genomic DNA was amplified using a REPLI-g kit (Qiagen Inc.), phenol extracted and ethanol precipitated. Three samples were prepared using 2.5 μg (micrograms) of amplified E. coli control genomic DNA and three different quantities of amplified L. cremoris sample genomic DNA (0.625 μg, 2.5 μg and 10.0 μg). The control and sample DNA was combined and subjected to DnaseI digestion such that that the final fragment size ranged from 50-200 bp. The fragment DNA was then end-labeled with Biotin-N6-ddATP using terminal transferase in preparation for hybridization.

Optimization Hybridizations And Scanning

Hybridizations were set up using 2.5 μg of E. coli genomic DNA and 3 different concentrations of L. cremoris genomic DNA: 0.625 μg, 2.5 μg and 10.0 μg, providing 0.25×, 1× and 4× dilutions. Two hybridizations were performed for each dilution under standard expression hybridization conditions, and three scans were performed for each array at varying photomultiplier tube voltage settings (PMTs), giving a total of 18 images (3 dilutions×2 replicates×3 PMT settings). The PMT voltages spanned a range of 100 V, in steps of 50, ensuring that one set of scans would capture the full data range without saturating the features. PMT1 was the middle setting, PMT2 was the high end, and PMT3 was the low end.

Data Normalization

Each image was extracted using NimbleGen's NimbleScan 2.0 software and saved as a NimbleGen PAIR file. Extraction was done on a per container basis. After extraction, the data in the PAIR file was combined and rearranged, so that each replicate block containing the ECOLI, RANDOM and LCRE was placed in a separate column in a single data file. Each set of data from the three different PMTs was treated separately. For each PMT a file was produced which contained the columns describe in Table 2.

TABLE 2

| COLUMN_NAME | DESCRIPTION |
|---|---|
| GENE_EXP_OPTION | ECOLI, LCRE, or RANDOM |
| SEQ_ID | EcoliK12, RANDOM.GC designation, or the L. cremoris SEQ_ID |
| PROBE_ID | Individual PROBE_IDs |
| POSITION | Position in the genome for E. coli, or position in the sequence for L. cremoris |
| CHIP_ID_PMT1_BLOCK1 | $1^{st}$ column of data for the experiment |
| CHIP_ID_PMT1_BLOCK2 | $2^{nd}$ column of data for the experiment |
| Etc. | Etc. |

Normalization was performed using R, a language and environment for statistical computing and graphics, and the vsn (variance stabilizing normalization) package from the BioConductor project (http://bioconductor.org). The "VSN package" functions to calibrate "sample-to-sample variations through shifting and scaling, and transforms the intensities to a scale where the variance is approximately independent of the mean intensity. The variance stabilizing transformation is equivalent to the natural logarithm in the high-intensity range, and to a linear transformation in the low-intensity range. In an intermediate range, the arsinh function interpolates smoothly between the two." For data normalization, the "*ECOLI*" and "RANDOM" probes were used to generate normalization parameters that were then applied to the entire data set.

After normalization, the *L. cremoris* probes were written out to text files for further processing. The normalized data file has the same column format as the raw data file, but only contains the information for the *L. cremoris* probes.

Calculation of Best-Fit Line To Dilution Series

The idea behind the optimization strategy is that the probes with the signal intensities that best follow the dilution series, and consistently have maximal brightness are to be selected as optimized probes. To find those probes, a weighted linear regression is fitted to the dilution series for each probe and the slope and correlation coefficient is calculated. A log2 transformation of the signal intensity and a weighted linear regression are used to minimize the effect of outliers on the data. The weights for the linear regression are calculated by fitting the line, calculating the residuals, and then using the weights from a tukey biweight mean calculation on the residuals to fit a weighted regression. At the same time, the tukey biweight mean of the signal intensities of the probe at the 4× dilution is calculated to represent the overall signal intensity of the probe. All of this information is then written to a text file. Table 3, shown below provides a description of data columns in this file.

TABLE 3

| COLUMN_NAME | DESCRIPTION |
| --- | --- |
| SEQ_ID | Unique identifier for sequence ID |
| PROBE_ID | Unique identified for probe ID |
| POSITION | Position of probe in parent sequence |
| WEIGHTED_SLOPE | Weighted slope of dilution series |
| WEIGHTED_R_SQUARED | Weighted correlation coefficient |
| INTENSITY | Tukey biweight mean of signal intensity from 4X dilution. |

Basis For Probe Optimization

Figure 2:
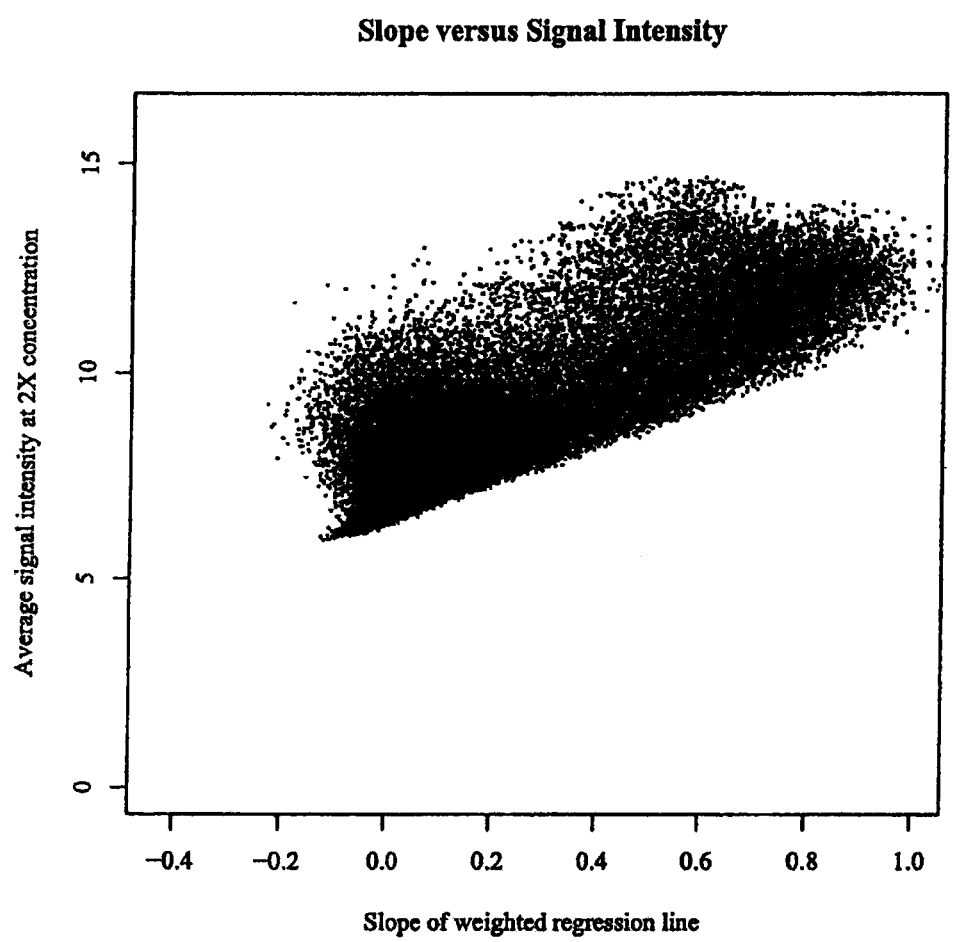
FIG. 2 is a graphical representation of a slope versus signal intensity plot showing that the brightest probes are not always the best at measuring the change in DNA concentration.
Figure 3:
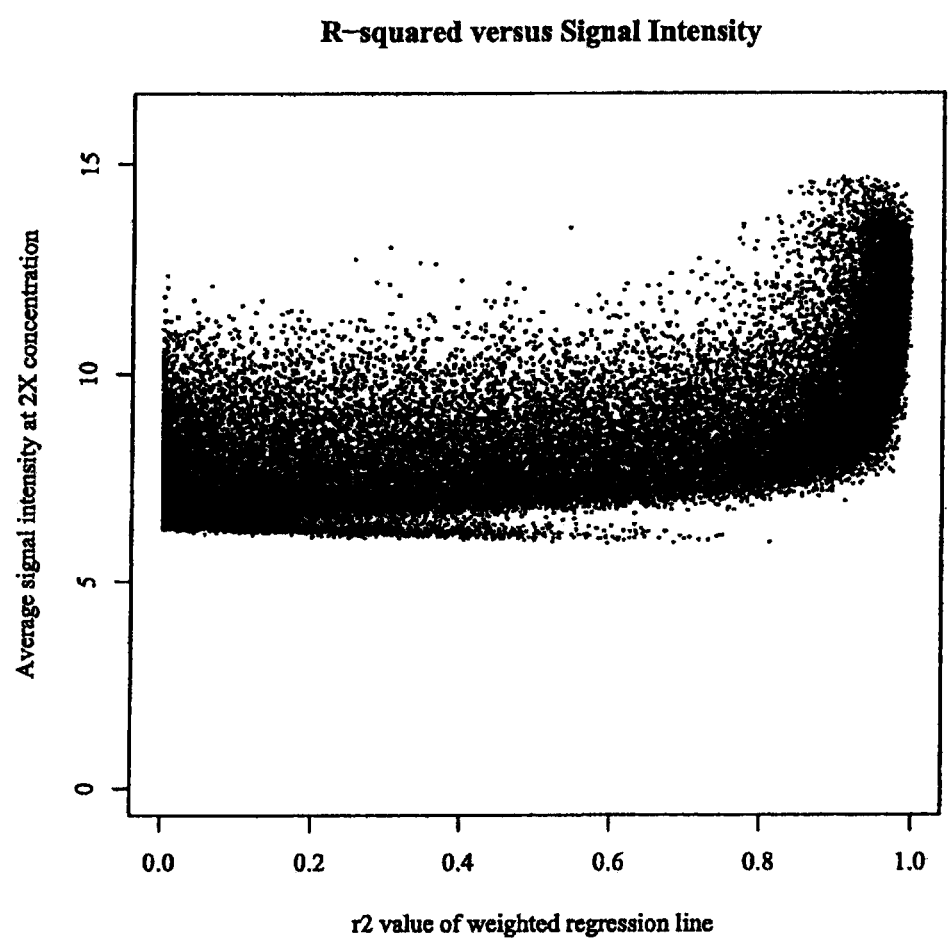
FIG. 3 is a graphical representation of an $r^2$ versus signal intensity plot showing that the brightest probes are not always the most reproducible.
Figure 4:
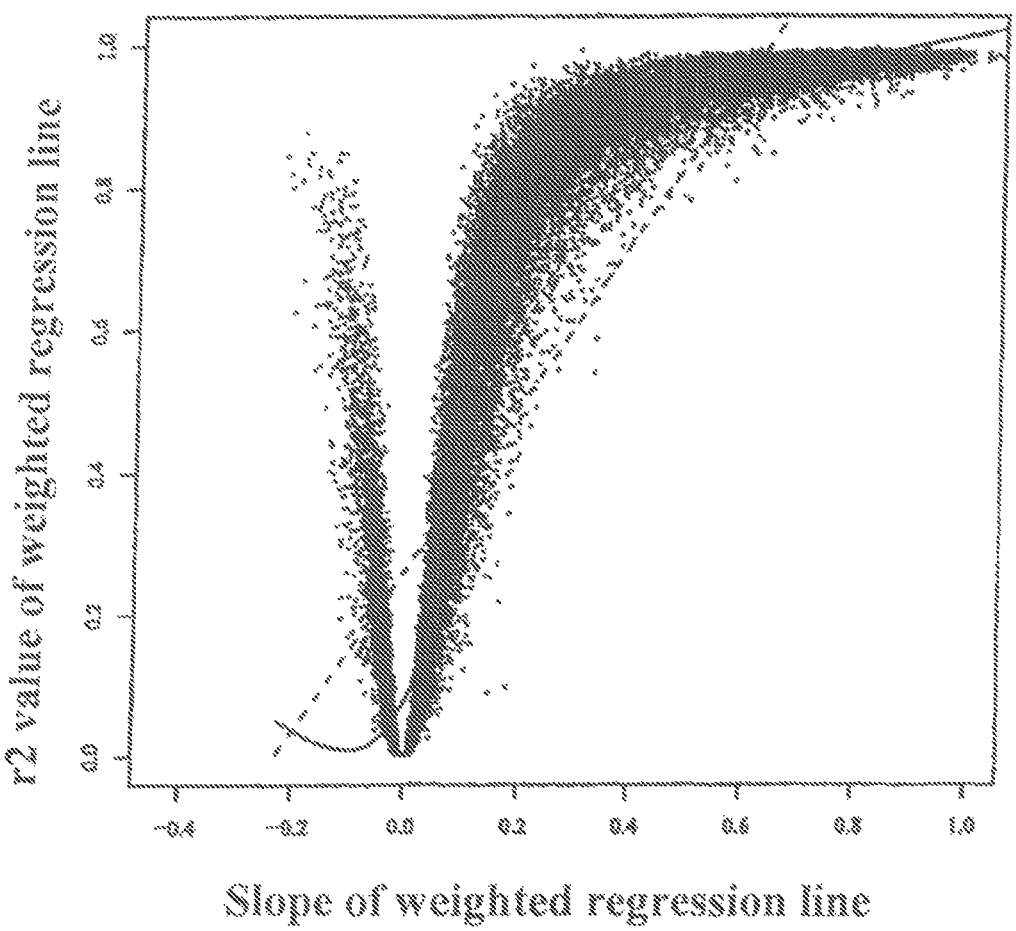
FIG. 4 is a graphical representation of a slope versus $r^2$ value of the weighted regression line for individual probes following the dilution series.

A common misconception in empirical probe optimization studies is that the probes with the brightest signal intensity are the best probes. The following plots demonstrate that this is often not the case. FIG. 2 shows that, on average, probes that lie in the middle range of signal intensities track with the DNA dilution series better than the brightest probes. FIG. 3 shows that probes in the middle to high-end range of intensities also tend to perform more consistently, as measured by the correlation coefficient of the regression line. FIG. 4 shows a scatterplot of the slope versus the $r^2$ value of the weighted regression line for individual probes following the dilution series. It shows that there are a large number of probes that meet criteria of consistent performance and ability to track with the DNA dilution series. The tail on the left is the result of negative slopes—indicating that there are probes that get dimmer as the DNA concentration rises. Some of the probes with negative slopes have $r^2$ values that are quite high. This may indicate that there is some type of competitive hybridization at work, since as the amount of *L. cremoris* DNA increases, the signal intensity of the probe decreases.

Selection of Optimal Probes

The weighted regression data was load into a MySQL database and optimal probes were selected using a modification of NimbleGen's rank selection algorithm. The weights for the various pieces of data were based on the plots above, and on the results from previous optimization experiments. The data from all three PMT settings was compared and found to be essentially the same. PMT2, the brightest of the data sets, was selected for the optimization, since the probe signal intensities have the greatest range. The detailed probe selection procedure was performed as described hereinabove.

It is also envisioned that the process of selecting optimal probes as described in this example (i.e., entering the regression data into a database, querying the database and selecting optimized probes) could also be performed using a "tab-delimited text file" rather than storing the data into a database and subsequently retrieving the data. Accordingly, the database as described herein is meant to be only a tool of convenience and not as a means for limiting the inventive method.

Results

Probe Set Overlap

FIG. 1 is a Venn diagram of the original set(s) of rank-selected probes with the final optimized set. The intersection of the original top 5 probes and the set of optimal of probes is approximately equal to what one would expect at random. This indicates that the initial in silico rank selection may be improved by the empirical hybridization data.

Plots Showing Optimal Probes

FIG. 2 shows that, on average, probes that lie in the middle range of signal intensities track with the DNA dilution series better than the brightest probes. FIG. 3 shows that probes in the middle to high-end range of intensities also tend to perform more consistently, as measured by the correlation coefficient of the regression line. FIG. 4 shows a scatterplot of the slope versus the $r^2$ value of the weighted regression line for individual probes following the dilution series. It shows that there are a large number of probes that meet our criteria of consistent performance and ability to track with the DNA dilution series. Therefore, the results ascertained from this experiment meet our expectations, with most of the optimal probes showing the highest slopes, large $r^2$ values, and medium relative signal intensity. In examining the plots, there are occasionally probes selected which do not meet the above criteria. In general, these probes belong to genes where all of the probes were non-optimal. This indicates that the final probes selected were the best of a bad lot, and it may not be possible to select good probes from this very small subset of genes. These probes/genes should be viewed with suspicion in any subsequent RNA hybridizations.

It is understood that certain adaptations of the invention described in this disclosure are a matter of routine optimization for those skilled in the art, and can be implemented without departing from the spirit of the invention, or the scope of the appended claims.

We claim:

1. A method for selecting optimized oligonucleotide probes for use in a hybridization-based assay from an original oligonucleotide probe set, the method comprising the steps of:

a) providing the original oligonucleotide probe set on a first and second hybridization array;

b) providing serial dilutions of a genomic sample, wherein the genomic sample is labeled;

c) hybridizing a first dilution of the labeled and serially diluted genomic sample to the first hybridization array, d) measuring a signal intensity produced for each of the probes;

e) hybridizing a second dilution of the labeled and serially diluted genomic sample to the second hybridization array;

f) measuring a second signal intensity produced for each of the probes;

g) computationally generating weighted regression data from the signal intensity produced for each of the probes;

h) entering the regression data into a database; and i) querying the database to select optimized probes which exhibit signal intensities that correspond to the serial dilutions of genomic sample, are reproducible, and are strong relative to other probes in the original probe set.

2. The method of claim 1, wherein the oligonucleotide probes are DNA or RNA.

3. The method of claim 1, wherein the hybridization-based assays are selected from the group consisting of microarray-based assays, bead-based assays, genotyping assays, and RNAi assays.

4. The method of claim 1, wherein the hybridization-based assays is a microarray-based assay.

5. The method of claim 4, wherein the microarray is synthesized by maskless array synthesis.

* * * * *